(12) United States Patent
Richardson

(10) Patent No.: US 6,381,013 B1
(45) Date of Patent: Apr. 30, 2002

(54) TEST SLIDE FOR MICROSCOPES AND METHOD FOR THE PRODUCTION OF SUCH A SLIDE

(75) Inventor: Timothy M. Richardson, Bolton (CA)

(73) Assignee: Northern Edge Associates (CA)

( * ) Notice: Subject to any disclaimer, the term of this patent is extended or adjusted under 35 U.S.C. 154(b) by 0 days.

(21) Appl. No.: 08/882,491

(22) Filed: Jun. 25, 1997

(51) Int. Cl.⁷ .................................................. G01J 1/10
(52) U.S. Cl. .................. 356/243; 356/305; 356/243; 356/388; 356/390; 356/391; 356/392; 356/393; 356/394
(58) Field of Search ................................. 356/243, 305, 356/388, 390–394

(56) References Cited

U.S. PATENT DOCUMENTS

| | | | | |
|---|---|---|---|---|
| 4,055,376 A | * | 10/1977 | Daberko ..................... | 350/10 |
| 4,616,241 A | | 10/1986 | Biefeld et al. ................ | 357/16 |
| 4,947,223 A | | 8/1990 | Biefeld et al. ................ | 357/30 |
| 5,027,178 A | | 6/1991 | Svilans ....................... | 357/30 |
| 5,608,519 A | | 3/1997 | Gourley et al. ............. | 356/318 |
| 5,622,796 A | | 4/1997 | Canestrari .................... | 430/22 |

FOREIGN PATENT DOCUMENTS

| | | | | |
|---|---|---|---|---|
| EP | 02141601 | 5/1990 | ........... | G01B/7/34 |
| FR | 2702277 | 9/1994 | .......... | G01M/11/00 |

OTHER PUBLICATIONS

Electro–Optical Systems Design; OTF Quantitative Image Analysis, David Smith, Dec. 1979.

Cambridge University Press; Nanofabrication And Biosystems, H. Hoch, L.W. Jelinski, and H.G. Craighead.

Development in Semiconductor Microlithography; Testing The Mann Type 4800DSW™, Wafer Stepper™, W. Schneider, vol. 174, pp. 6–14 (1979).

"Nanofabrication And Biosystems" by H.C. Hoch, L.W. Jelinski, and H.G. Craighead; JENOPTIK, Laser Optik Systeme; and "Contrast Transfer In Confocal Microscopy" by R. Oldenbourg, et al.

* cited by examiner

*Primary Examiner*—Frank G. Font
*Assistant Examiner*—Reginald A. Ratliff
(74) *Attorney, Agent, or Firm*—Fitzpatrick, Cella, Harper & Scinto

(57) ABSTRACT

A test slide for the calibration, characterization, standardization, use and study of photon and electron microscopes. The slide is created by forming patterns with specific types of geometries on suitable substrates and these slides provide a standard for comparison of image forming capability of any type of microscope imaging system including, without limitation, light, UV, and X-ray photon microscopical imaging systems operating in transmission or reflection modes, and other microscope techniques. Microscopists can employ one of these slides to compare images of the slide which have been produced by the microscope system under consideration with a known, accurate, image of the slide to better understand the fidelity and accuracy of the microscope system under consideration. The test patterns can also comprise reference images which can be images created by a graphic artist or the like or which can be actual images of samples, these images being either two dimensional or three dimensional.

23 Claims, 11 Drawing Sheets

“The Great Age of the Microscope”, Gerard L'E Turner, 1989, First Edition, as published by the Royal Microscopical Society, pages 344–345 and in "Micrographia Historica— The Study of the History of the Microscope", by the same author, 1972, published by the Royal Microscopical Society, pages 20–24.

TEST SLIDE FOR MICROSCOPES AND METHOD FOR THE PRODUCTION OF SUCH A SLIDE

FIELD OF THE INVENTION

The present invention relates to the calibration, standardization, use and testing of microscopes. More particularly, the present invention relates to a test slide and to methods of production and use thereof.

BACKGROUND OF THE INVENTION

As is known, microscopes must be tested to ensure that the images observed with the microscope are accurate and/or understood. In particular, the resolving power, the image formation capabilities and the aberrations of microscopes and their related optics must be determined and documented before reliance can be placed on the observed images obtained therewith. Generally, the testing of a microscope can comprise a set of one or more characterizations and/or calibrations. For example, characterization tests can be performed to determine the depth of field, flatness of field, aberrations and illumination characteristics within the field of view of a microscope at various magnification settings. Also, calibration tests can be performed to determine the actual magnification levels, measure the amount of any observed aberrations, etc.

Conventionally, microscopists and microscope manufacturers have experienced difficulty in locating naturally occurring or artificial structures with suitable known and reproducible features to employ as test specimens for microscope testing. It has also been difficult to find test specimens that yield information on the means by which microscopes form their images. This latter factor is important as these means often have limitations such that the resolution and imaging of objects with differing geometries may not be comparable, due to the methods of image formation or physical limits of the optics in the microscope. In some cases it has been noted that seemingly properly formed images will in fact be completely erroneous due to effects of optical interference or limits in the optics due to aberrations, etc.

Early previous attempts to manufacture suitable test systems have primarily consisted of ruled gratings of uniformly spaced parallel lines scribed in the surface of a substrate by a stylus, such as a diamond point. These ruled substrates have been produced to address the need for resolution testing standards for light microscopes and such gratings are commonly employed as diffraction gratings for spectroscopic applications.

Such gratings were developed most notably by F. A. Norbert in Germany in the mid to late 1800's, as described in "The Great Age of the Microscope", Gerard L'E Turner, 1989, First Edition, as published by the Royal Microscopical Society, pages 344–345 and in "Micrographia Historica— The Study of the History of the Microscope", by the same author, 1972, published by the Royal Microscopical Society, pages 20–24.

Norbert manufactured ruled gratings that were used in tests of microscope objective performance and he eventually ruled a grating with a spacing between the grating lines of 0.13 microns (i.e.—from the trough of one line to the trough of the next line), although the proof of this spacing had to await the development of the electron microscope as this spacing was too small to be resolved using traditional light microscope means.

Norbert's standard offering was produced as a series of graded gratings ranging from a course grating to a fine grating arranged on a cover slip which was then mounted to a standard microscope slide. These slides were sold as test slides and became a relatively accepted means of comparing the performance of microscopes.

Since Norbert's time, there have been few other attempts to produce such similar test slides and there has been no attempt of which the present inventor is aware to produce a comprehensive industry-standard test slide. It should also be noted that diffraction gratings are still not commercially available with sufficiently close spacings to test the resolving power of the best light microscopes which are now available.

Instead, the standard means of testing microscopes at the time of Norbert, and one still in use today, is to use a diatom as a test specimen, as diatoms have periodic structures as part of their features and these periodic structures provide a somewhat known set of optical characteristics and geometry. The two most common diatoms used for this purpose are the *Amplipleura Pellucida* and *Pleurosigma Angulatum*. While commonly employed as test specimens, diatoms still leave much to be desired as there is some variation from diatom to diatom and their exact appearance is not known, rendering their use for calibration and characterization purposes difficult at best.

Most recently, nanofabrication techniques have been employed to produce test slides and these are described by Rudolf Oldenburg et al. in, "Standard Test Targets For High Resolution Light Microscopy", Nanofabrication and Biosystems, Cambridge University Press, 1996, pages 123–138, and in "Image sharpness and contrast transfer in coherent confocal microscopy", Journal of the Royal Microscopical Society, 172, pages 31–39, 1993. These references describe slides with test images produced by the use of focused electron beam directwrite photo-lithography techniques and direct etch micromachining techniques, the slides being useful for visible light microscopy.

However, several problems exist with the Oldenburg slides. For example, the slides are only useful with visible light microscopes and are not suitable for UV, IR, etc. microscopes. Also, due to the method of their fabrication, these slides are very expensive and time consuming to manufacture. Also, the test patterns employed on these slides are limited to artificial constructs such as Siemens stars, gratings, etc.

It is desired to have a test system which is superior to the prior art systems described above and which produces an accurate and repeatable means of comparing microscope performance and of assessing image formation capabilities and image formation theory.

SUMMARY OF THE INVENTION

It is an object of the present invention to provide a novel test slide for microscopes. It is a further object of the present invention to provide a novel method of manufacturing a test slide for microscopes.

According to a first aspect of the present invention, there is provided a test slide comprising:

a substrate;

a test pattern formed on said substrate, said pattern comprising at least a diffraction grating and a scale system; and a locating pattern formed on said substrate to assist an observer to locate said test pattern.

According to another aspect of the present invention, there is provided a method of manufacturing a test slide, comprising the steps of:

(i) providing a substrate with an image area;

(ii) coating at least a portion of said image area with a resist compound;

(iii) exposing said resist compound to form a test pattern and a locating pattern thereon;

(iv) developing said resist compound and removing portions of said resist compound from said substrate to form said test pattern and a locating pattern thereon.

According to yet another aspect of the present invention, there is provided a test slide comprising:

a substrate including an image area;

a test pattern formed on said substrate in said image area, said pattern comprising a known image having at least two or more features selected from the group comprising grating-type structures, scale systems, image series, offset segment pie stars and indicia to uniquely identify said slide.

According to yet another aspect of the present invention, there is provided a test slide comprising:

a substrate;

a test pattern formed on said substrate, said pattern having known shape and size; and a protective layer on said test pattern, said layer inhibiting inadvertent damage to said test pattern and being non-opaque to an preselected range of wavelengths for which said slide is intended to be used.

According to yet another aspect of the present invention, there is provided a method of forming a test slide for microscopes, comprising the steps of:

(i) forming a master test pattern on an information carrier for an injection molding device, said test pattern including patterns of known size and shape;

(ii) inserting said information carrier into said injection molding device;

(iii) cycling said injection molding device to inject liquefied resin into contact with said information carrier and to cool said resin to form a plastic carrier with said test pattern formed in one surface; and (iv) removing said plastic carrier from said injection molding machine.

According to yet another aspect of the present invention, there is provided a method of forming a test slide for microscopes, comprising the steps of:

(i) forming a master test pattern on an information carrier for a mold, said test pattern including patterns of known size and shape;

(ii) inserting said information carrier into a mold;

(iii) adding a substrate material to said mold to contact said information carrier and setting said substrate material to form a carrier with said test pattern formed in one surface; and (iv) removing said carrier from said mold.

BRIEF DESCRIPTION OF THE DRAWINGS

Preferred embodiments of the present invention will now be described, by way of example only, with reference to the attached Figures, wherein.

DETAILED DESCRIPTION OF THE INVENTION

Figure 1:
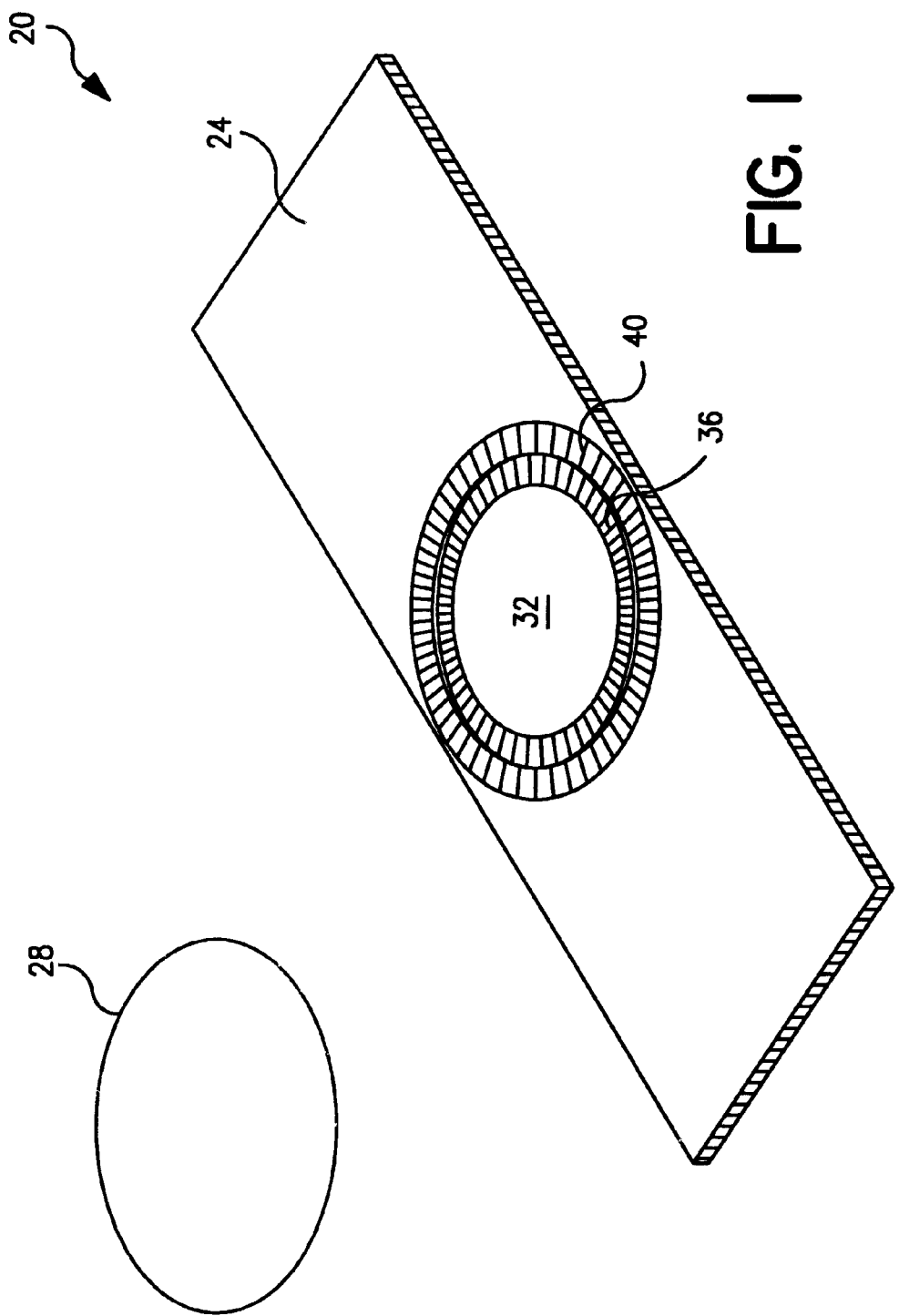
FIG. 1 shows an exploded perspective view of a test slide in accordance with an embodiment of the present invention.

The components of a test slide in accordance with an embodiment of the present invention are indicated generally at 20 in FIG. 1. As used herein, the term "test slide" is intended to comprise a substrate having a test pattern suitable for calibrating and/or characterizing microscopes, and/or comprising reference images useful therewith. As used herein, the term microscope is generally intended to comprise instruments for forming a magnified image of a sample, whether by photons (visible, IR, NIR or UV or the like) or electrons (scanning electron microscopes, etc.).

In the embodiment of FIG. 1, test slide 20 comprises a microscope slide base 24 and a cover slip 28. A locating and test pattern, described below in more detail, is formed on the side of cover slip 28 adjacent slide base 24. Slide base 24 includes an image area 32 which is surrounded by a expansion volume 36 and an adhesive ring 40. A more detailed description of slide base 24 is given in co-pending U.S. Patent application serial number. to the present inventor and assignee of the present invention and the contents of that application are incorporated herein by reference.

Cover slip 28 is preferably mounted to slide base 24, with the locating and test pattern over image area 32 and with a layer of a suitable immersion or mounting fluid (not shown) therebetween. Cover slip 28 is maintained in place on slide base 24 and the immersion or mounting fluid is sealed from escaping or interaction with the ambient environment by adhesive ring 40. Any excess immersion or mounting fluid from the image area is contained in expansion volume 36. As will be apparent to those of skill in the art, adhesive ring 40 can be located on cover slip 28 rather than on slide base 24, if desired. As will also be apparent to those of skill in the art, if a two part adhesive, such as an epoxy, is employed, an adhesive ring of one part can be provided on cover slip 28 and an adhesive ring of the other complementary part can be provided on slide base 24.

As will also be apparent to those of skill in the art, cover slip 28 need not be circular and can be any suitable shape such as rectangular or square. In such a case, expansion volume 36 and adhesive ring (or rings) 40 will have a corresponding shape.

Figure 2:
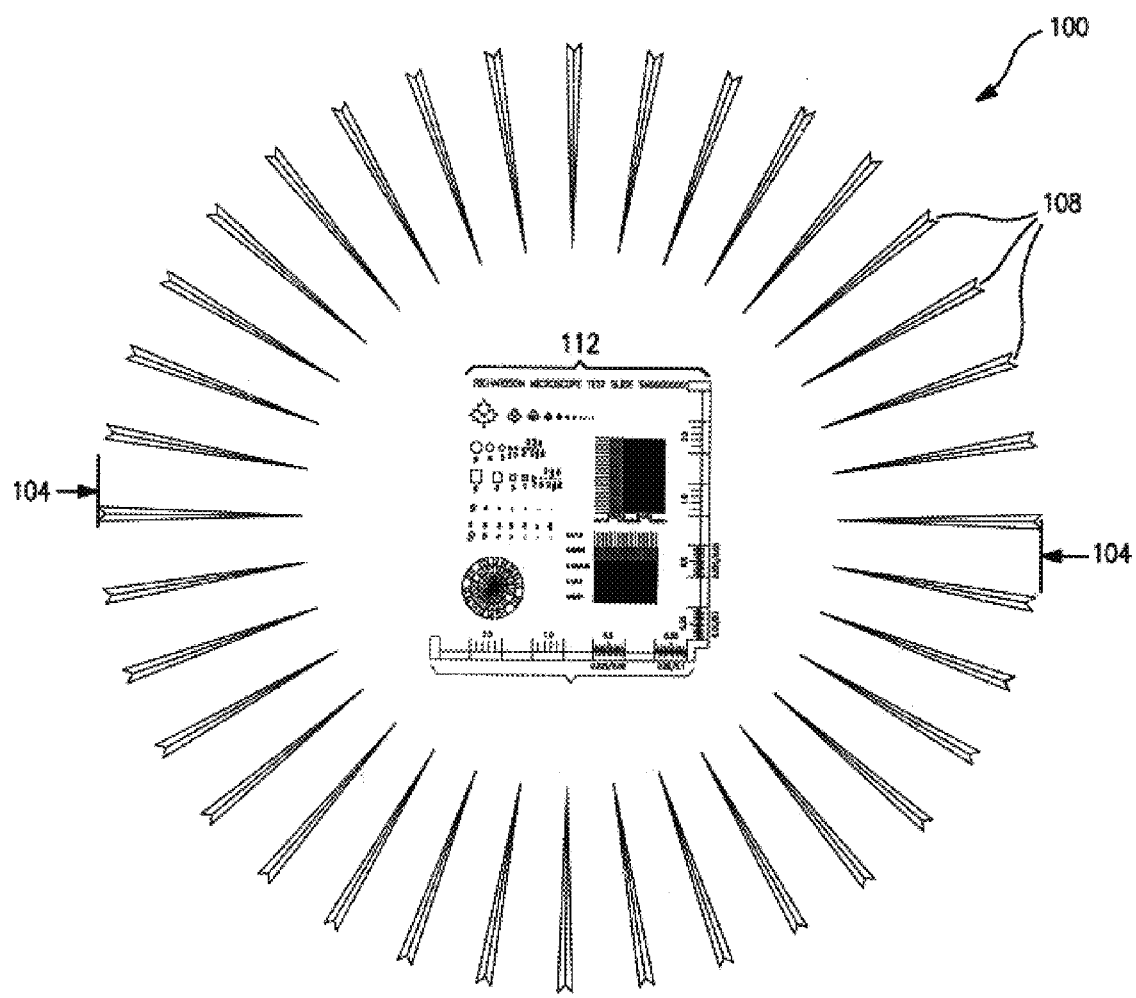
FIG. 2 shows a locating and test pattern for the slide of FIG. 1.
Figure 3:
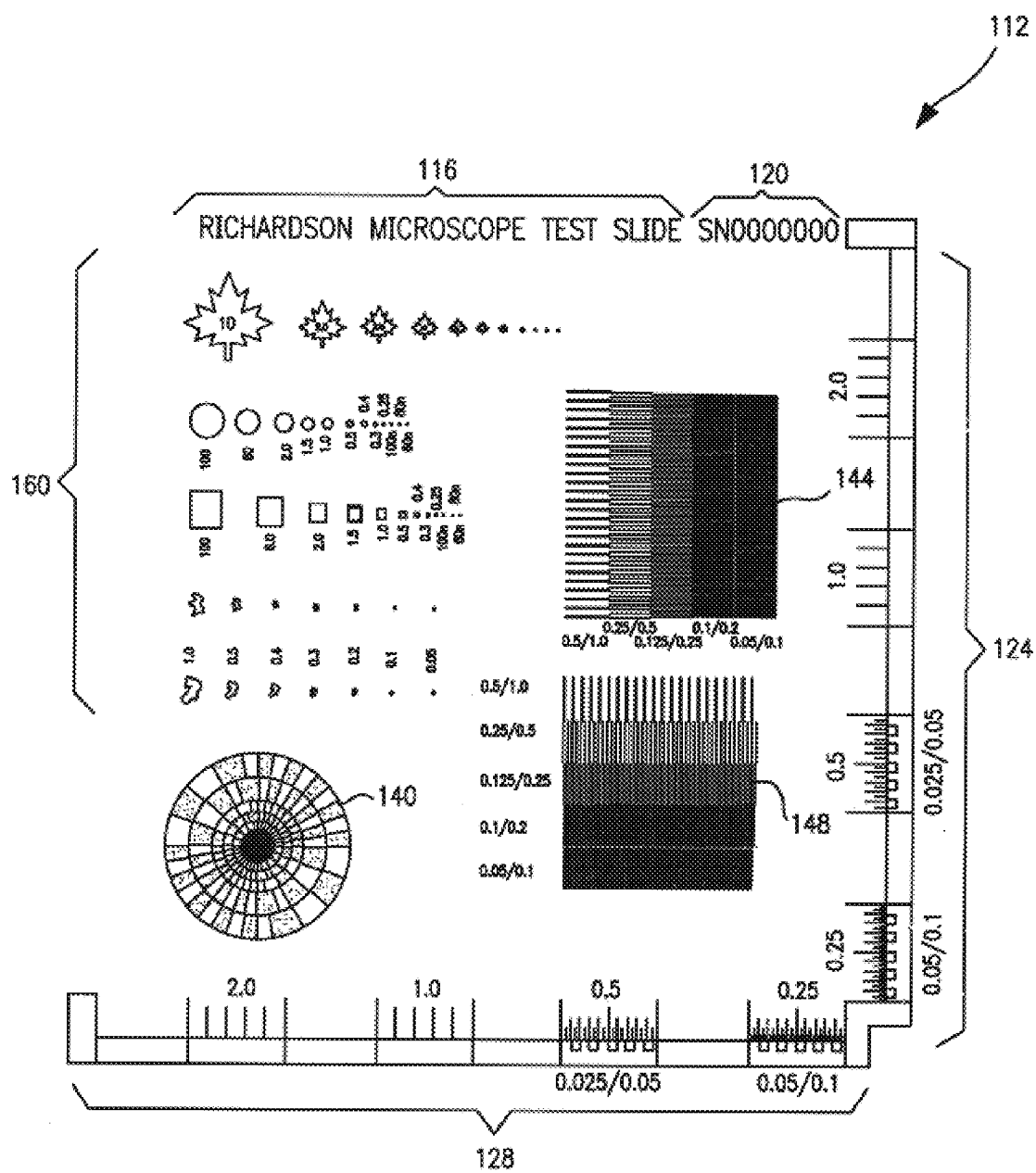
FIG. 3 shows the test pattern which forms part of the locating and test pattern of FIG. 2.

FIG. 2 shows a locating and test pattern 100 for test slide 20. In a present embodiment, the diameter 104 of the complete locating and test pattern 100 is typically about two hundred and fifty to about three hundred microns. Pattern 100 includes a locating pattern 108, such as the illustrated "sunburst" pattern of arrows in FIG. 2, to allow the user to quickly locate a central test pattern 112, which is shown in more detail in FIG. 3. In the embodiment of FIGS. 2 and 3, central test pattern 112 comprises a substantially square area, measuring about ninety microns square. As will be apparent to those of skill in the art, other geometries and/or sizes can be employed for central test pattern 112 if desired.

As shown in FIG. 3, central test pattern 112 includes standard header information 116 and a serial number 120, if desired, which can be used to track the providence and calibration documentation of any particular slide 20. A vertical scale system 124 is provided. In the embodiment shown in the Figures, scale system 124 includes divisions ranging from twenty-five nanometer lines on fifty nanometer spacings up to ten micron solid bars with many available reference scales in between these two extremes of size. In the embodiment shown in the Figures, vertical scale 124 is complemented by an identical horizontal scale system 128 with the same pattern features and these scale systems are shown in more detail in FIG. 4. Together, scale systems 124 and 128 form the basis of the calibration aspect of the function of slide 20.

Figure 4:
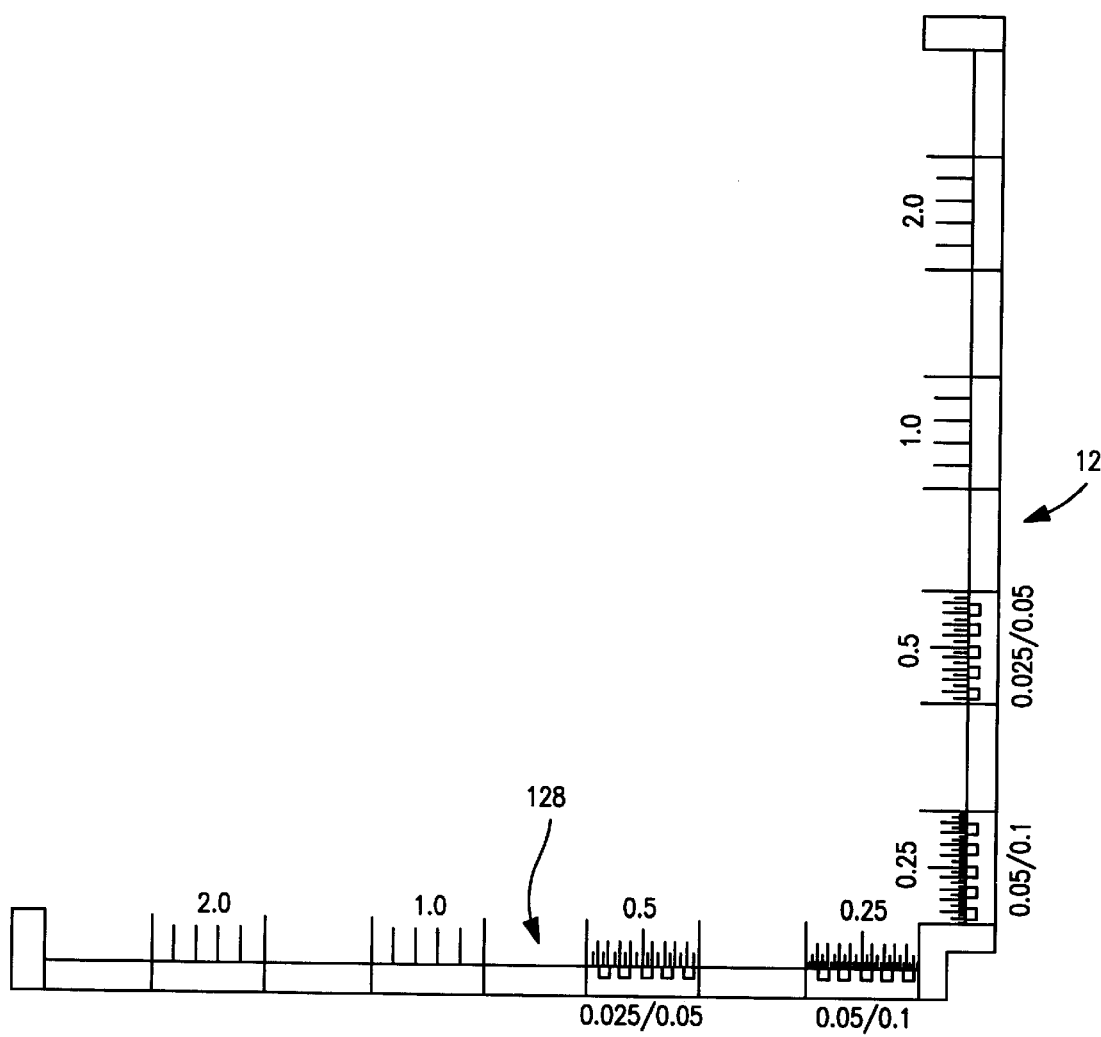
FIG. 4 shows the horizontal and vertical scale systems included in the pattern of FIG. 3.

As will be apparent to those of skill in the art, scale systems 124 and 128 can be provided with a variety of pattern features and scale system 124 need not provide the same pattern features as scale system 128, although this is presently preferred. As shown in FIG. 4, vertical scale 124 and the horizontal scale 128 preferably include fine 132 and super fine 136 scales.

Central test pattern 112 also includes an offset segment pie star 140 which contains various pie-shaped segments which decrease in size as the pattern nears its center. As is known, this pattern is very effective for testing flatness of field, resolution and other optical aberrations.

Central test pattern 112 also includes a series of grating-type structures 144, which can either be alternating opaque and transparent bars or etched lines. As used herein, the term "grating" or "grating-type" structure is intended to comprise any ruled or other repeated series of equally spaced features and are not intended to be limited to diffraction gratings.

Figure 5:
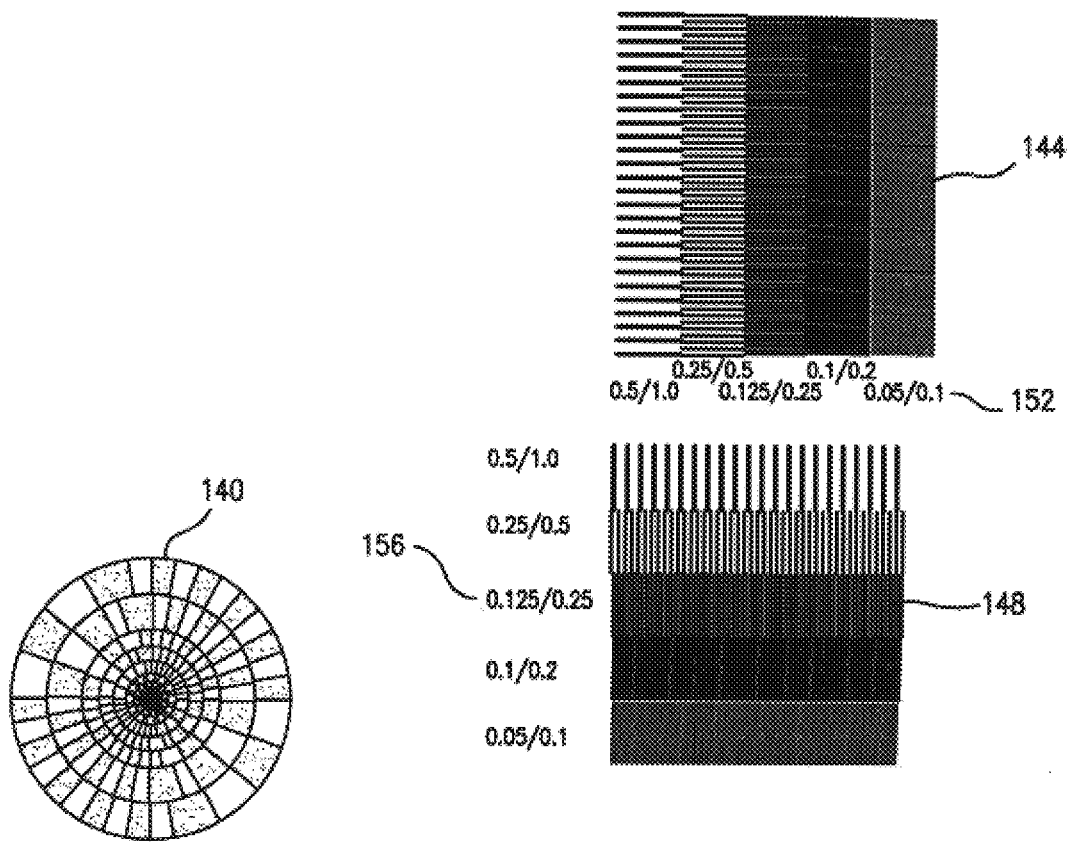
FIG. 5 shows grate-like structures and a key pie structure included in the pattern of FIG. 3.

A matching, but vertical, series of grating-type structures 148 is also provided. The spacing of the structures 144 and 148 preferably ranges from five hundred nanometer bars on one thousand nanometer spacings to fifty nanometer bars on one hundred nanometer spacings and finer spacings can be provided, if desired. Pie star 140 and structures 144 and 148 are shown in more detail in FIG. 5 wherein the scale reference tests 152 and 156 for structures 144 and 148, respectively, are also shown.

Central test pattern 112 also includes a set 160 of series of identical patterns of decreasing sizes and these are intended to provide the basis for many of the educational and test aspects of slide 20. Set 160 is shown in more detail in FIG. 6 wherein a series 164 of complex geometrical patterns, shown here as maple leaves, are provided for resolution and image formation testing. The size 168 of each particular pattern in series 164 is also indicated in pattern 112.

Figure 6:
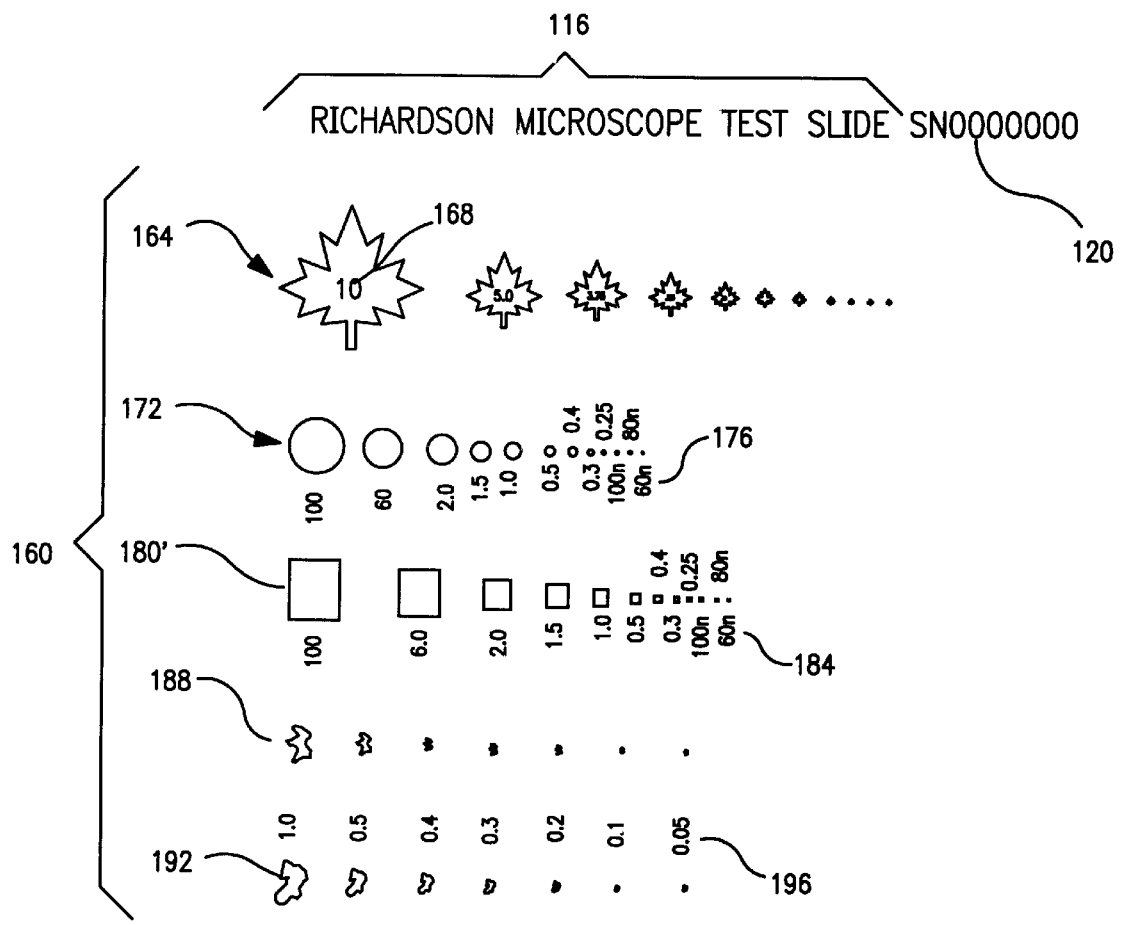
FIG. 6 shows a set of series of patterns included in the pattern of FIG. 3.

As also shown in FIG. 6, set 160 includes a series 172 of solid circles (or apertures in a negative image pattern) which can be used for studying diffraction effects and "airy disc" patterns. As with series 164, the size 176 of each pattern in series 172 is indicated in pattern 112. Set 160 also includes a series 180 of solid squares (or square apertures in a negative image) which can be used for comparison with the images produced by series 176 of circular features, described above and the size 184 of these solid squares is also indicated in pattern 112.

Set 160 also includes a series 188 of irregular shapes with pointed edges, which can be used for studying the limits of resolution approaching pointed features, and a similar series 192 of irregular but rounded edge shapes which can be used for comparison purposes. The size 196 of the patterns in series 188 and 192 are also indicated in pattern 112. In series 188 and 192, rather than indicating an absolute size measurement, size 196 indicates a relative size. Specifically, in this example, the first patterns of each series are shown with a size of 1.0 and the second pattern of each series, which is one half the size of the first corresponding pattern, is shown with a size of 0.5, etc.

FIG. 6 also shows a typical header information line 116 and serial number 120 which would be unique to each slide, as mentioned above.

As will be apparent to those of skill in the art, the present invention is not limited to use with the particular embodiment of central test pattern 112 discussed above, and it is contemplated that a variety of other patterns could also be employed, if desired, such additional patterns providing a useful set of test features, preferably including at least a subset of the test pattern features described above. Similarly, it is contemplated that other locating patterns, in addition to or instead of locating pattern 108, can also be employed as will occur to those of skill in the art.

Locating pattern 108 and central test pattern 112 discussed above and shown in the attached Figures can be created in either a positive or negative process. In other words, the patterns can be either transparent or opaque against a complementary background. The patterns can also be created by image-forming compounds or layers where differential refraction, reflection, phase delay or color are used to create the contrast of the image.

While the discussion above focuses on an embodiment of slides 20 which include cover slip 28, it will be apparent to those of skill in the art that cover slip 28 is not required for some intended uses of slide 20 and pattern 100 can be directly formed on image area 32 of slide base 24 and slide 20 employed without any cover slip 28. In such a case a protective layer, which is transparent at the wavelength and magnification levels of the microscope to be tested, can be provided on top of locating and test pattern 100. Suitable protective layers, and methods of forming them, are described below.

Test slide 20 is intended to be used as a new standard for testing and assessing the performance of microscopes, for use in educational studies of microscopes to demonstrate the method of image formation, and as a means of intercomparison between microscopists working with microscopes at different locations where it is necessary to use a standard slide to compare the scales or resolving power of two or more different microscopes. In particular, slide 20 is intended to be a meteorological standard in that it can be used for calibrating the microscope as to distances in the x, y, and in some cases discussed in more detail below, z directions. It is also intended to be used as a means of assessing the flatness of field that a microscope can accomplish across its field of view. It is also intended to be used as a resolution test to determine the resolving power of the microscope in terms of how small an object it can resolve and what details it can provide about a small object of known geometry.

Another contemplated use of slide 20 is to assess the detectability limit of a microscope in terms of the ultramicroscopic techniques used with either ultramicroscopic illumination or dark field illumination where tiny objects much smaller than the normal resolution limit can be imaged by the action of light reflecting off the object as opposed to a true case of resolution. A typical case of ultramicroscopic imaging is the detection of particles in a very dilute colloidal suspension. Such a colloidal suspension can be simulated by forming small (for example, ten nanometer) pits in the surface of the slide, the pits being spaced at a distance which is very large relative to their size. Slide 20 is also to be used for studies of the exact nature of resolving power of a microscope where, instead of resolving regular structures, it is used to attempt to resolve known but irregular structures. Another contemplated use for slide 20 is for the calibration, characterization and study of the effect of aberrations and of the microscopic optical system on image formation in an electron microscope, or a near field scanning microscope, or any other type of high magnification imaging system.

Slide base 24 and cover slip 28 may be formed of many different types of material, depending on the intended application, as will be apparent to those of skill in the art. It is contemplated that the most common version of slide 20 will be fabricated using a high quality optical glass such as BK7, available from Schott Glass Technologies, 400 York Avenue, Duryea, Pa., USA or one of the heavier flint glasses such as LaSF 9, as available from Schott Glass Technologies. For work in the ultraviolet, it can be desirable to fabricate slide 20 of fused silica or of quartz crystal material that transmits in the ultraviolet. For use with deep ultraviolet, it is contemplated that slide 20 can be fabricated from calcium fluoride or lithium fluoride or barium fluoride based glasses or sapphire or any other suitable material, as will occur to those of skill in the art of UV and vacuum optics.

When fabricating slide 20, especially for use at high numerical apertures, the refraction indices of slide base 24, cover slip 28 (if any), the coupling fluid, the thickness of each component (particularly the cover slip or cover coating and the passivating layer, if any) should all be considered, and the selection of appropriate materials and/or combinations of materials will be apparent to those of skill in the art.

Due to hardness and toughness considerations it can be desired to fabricate slides 20 from sapphire or fused silica and thus provide a stable and durable test slide with a wide useful optical range, extending into the UV.

Where it is desired to use slide 20 in the UV portion of the spectrum, pattern 100 can be etched into or deposited on the surface of slide 20 by any means described herein, or by any other suitable means as will occur to those of skill in the art. In such a case, a protective planar over coat layer consisting of silicon dioxide or magnesium fluoride, either passivated with silicon dioxide or left bare, can be formed on pattern 100 in place of cover slip 28. As used herein, the term planar layer is intended to comprise a layer which has a substantially flat top surface irrespective of the geometry of the features on the bottom surface of the layer. This planar over coat layer can also be formed with a suitable varnish, lacquer or polymer coating, or it can be a thin cover slip 28 of fused silica or other material. It is important to note that, in this embodiment of the present invention, pattern 100 is formed on slide base 24 instead of more fragile cover slip 28 (even if present). A UV contrast enhancement for slide 20 can comprise thin films of tantalum oxide, titanium oxide, niobium oxide, carbon, or hafnium oxide or other suitable materials as will occur to those of skill in the art. Such contrast enhancement layers can be deposited by chemical vapor deposition (CVD) methods as part of the image formation process as described in more detail below. The contrast enhancement layer can be selectively removed, left intact or formed as a planar coating, depending upon the application, by any suitable process as will occur to those of skill in the art.

When it is desired form pattern 100 directly on slide 20 for use in IR, slide base 24 can be formed from a suitable IR transmitting material such as BK7 glass or fused or crystalline quartz, for near infrared, and silicon, germanium or similar IR transmitting materials for a broader IR range. Pattern 100 is then etched into or deposited onto slide base 24 via any suitable one of the methods described herein or via any other suitable method as will occur to those of skill in the art. Contrast enhancement can be provided by materials normally opaque to near infrared and IR, such as organic or polymer thin films, metal oxide thin films or other suitable materials as will occur to those of skill in the art and processed as described above.

For both the UV and IR embodiments, photoresist itself can often be employed as an effective contrast enhancement as it is often opaque, or can be dyed to be opaque in visible, UV or IR with non-bleaching absorbers such as carbon or inorganic pigment materials.

The above-described methods allow the creation of a test slide 20 with pattern 100 formed on a fused quartz slide base 24 with contrast enhancement and a chemical vapor deposited protective layer, which test slide 20 is suitable for use over a range of wavelengths from less than about one hundred and sixty nanometers to over about three thousand nanometers.

In the following discussion, it has been assumed that test pattern 100 is being formed on one side of cover slip 28 which serves as a substrate. The modifications required to form pattern 100 on a slide base 24, which serves as the substrate, will be apparent to those of skill in the art and will not be discussed further herein.

As discussed below in detail, the formation of pattern 100 in slide 20 is accomplished using known techniques commonly employed in semiconductor fabrication processes. These techniques are well known and are discussed and explained in a wide variety of sources.

Cover slip 28 can either be coated or uncoated at the beginning of the manufacturing process. In the event that it is desired to provide a high contrast embodiment of slide 20, cover slip 28 can be pre-coated with a metal such as chromium or aluminum or gold with suitable passivation layers consisting of silicon dioxide or other passivation means being included between the substrate slide and the deposited metal layer. It can also be desirable to overcoat the metal with the passivation layer. For example, in the case of aluminum, it may be desirable to passivate it with silicon dioxide or with magnesium fluoride or another antireflection coating. It will be apparent that such an anti-reflection coating can be selected for visual, UV, NIR, X-ray or other wavelengths or combinations of wavelengths, as appropriate.

Once the base material of cover slip 28 has been chosen and the decision has been made whether or not to coat it with a metal, cover slip 28 is prepared with a suitable resist material in a known technique, such as the coating system used in semiconductor manufacturing or a "spun on" resist system. As will be apparent to those of skill in the art, the resist can either be an optically transparent resist or it can be a dyed resist wherein the resist contains a dye or other components which heavily absorb in regions of the spectra which slide 20 will be used in. As another alternative, slide 20 can be coated with an optically black, thin film interference system wherein the interference system heavily absorbs in the target region of the spectra which will be used with slide 20. For example, for slides 20 intended for use with UV it is possible to create a thin film interference layer system which will absorb all light or a substantial portion of the light from about two hundred nanometers to about four hundred nanometers and provide a very optically black coating.

In general, the process used to manufacture slide 20 is to prepare the cover slip 28 by polishing and cleaning to obtain both a very fine surface finish with no scratches or contamination and, preferably, a very controlled thickness. While the former parameter is important for all applications, the latter parameter controls the focus point of slide 20 and is articularly desirable if slide 20 is to be used with an autofocus stage or the like. As will be apparent to those of skill in the art, the polishing and cleaning step will also result in slide base 24 and cover slip 28, if present, having suitable flat and parallel surfaces.

The next step is to coat cover slip 28 with the materials that are required, being metals or resist or optically black coatings, and to then suitably expose cover slip 28 with a desired image, such as pattern 100. This exposure can be accomplished using any suitable method, as would occur to those of skill in the art, including known mask and exposing systems (UV, X-ray, etc.) or energy beam exposure systems, such as focused ion beam or e-beam systems. Next, the resist is developed and baked to harden the resist.

Cover slip 28 can then be combined with a slide base 24, as described above, to obtain slide 20. Slides 20 prepared in this manner simply use the developed resist to provide pattern 100.

If it is desirable to provide a deeper set of contours on pattern 100, the cover slip 28 can be coated with the resist which is exposed, developed and then etched, using either dry etch or wet etching techniques, to create features in the substrate below the resist. As will be apparent to those of skill in the art, the method, rate of etch and etch chemistries can be controlled in order to produce either an undercut or angular set of image features in the material underneath the resist, resulting in pattern 100 having features in the x, y and z directions. For example, a set of concentric rings, whose depth increases as the center of the set is approached, can be provided to allow z-axis calibration and characterization studies.

After the etching process is completed, the etch resist can be left in place or it can be stripped from cover slip 28 all together, leaving just the etched details on the surface of cover slip 28. In the case wherein the etch resist will be left in place, it can have useful dyes added to it, to allow it to fluoresce at the wavelength of light used to image the completed slide, etc.

Another method to produce slide 20 is to use a focused energy beam to directly etch the patterns into cover slip 28 and this is presently believed to be most suitable for systems involving metallic or thin film interference layers deposited on top of the cover slip 28 wherein the focused energy beam system directly forms the image by ablating the chromium or aluminum metalization layer or the optically black layers. Alternatively, it is contemplated that the focused energy beam can be used to directly etch the surface of cover slip 28 itself without the etch resist step. This direct write approach can be used to form pattern 100 on cover slip 28 or on slide 20, either with or without layers of metalization, dielectric or passiviation.

Yet another method of producing slides 20 is to coat the cover slip 28 with an etch resist and then to expose and develop it. Next, metalization of a combination of the etch resist and the removed portions of the etch resist is performed, leaving metalization on the substrate and on the etch resist. Next, the etch resist and any metalization on the etch resist is selectively stripped from the slide, leaving metalization on the slide itself.

Yet another method of producing slide 20 is to employ known semiconductor epitaxy techniques to "grow" locating and test pattern 100 or to employ a laser of suitable wavelength to form a desired pattern.

Yet another method of manufacturing slides 20 is to coat cover slip 28, expose and develop the resist, etch back cover slip 28, remove the etch resist, metallize the entire system while producing metalization in the resist portions as well as on the surface of cover slip 28 which was previously covered by the resist and to then polish the surface of cover slip 28 removing the metalization on the surface and leaving metalization in the etched recesses of cover slip 28. A modification to this technique is to image and develop the photoresist and then metalize over the photoresist and pattern in the image area. Then the resist is removed with a suitable solvent which removes both the resist and the metal over it, thus forming the pattern in the absence of metal in the metalized area of the slide itself.

As an example of the scale of features which slides 20 are intended to be capable of incorporating, using focused energy beam technology, it is possible to produce slides 20 with fifty nanometer center-to-center spacing on a grating-type structure. It is also possible to produce one hundred nanometer diameter hole using focused energy beam technology. Further, focused energy beam techniques can be combined with standard semi-conductor photo-lithography techniques wherein the semi-conductor techniques produce structures of down to one micron and the focused energy beam produces the required smaller structures in selected areas.

The methods described above are intended to produce slides 20 with high degrees of repeatability and accuracy at reasonable costs. These methods are designed to produce slides 20 through a process of mass production wherein each slide 20 will match the previous slides to a significant degree, such that differences (if any) between slides 20 will not be discernable to microscopists.

It is contemplated that, much like semiconductor dies, a number of slide bases 24 or cover slips 28 can be prepared on a common substrate. This common substrate is then "waxed down", for example, to a mount and sawed into individual slide bases 24 or cover slips 28 and the wax mountant is removed leaving each slide base 24 or cover slip 28 as an individual area, free of the substrate.

The mounting of slides 20 provides a number of challenges. If it is desirable to use slide 20 in a low magnification, dry, microscopic system, pattern 100 can be formed on the upper surface of slide base 20, with no cover slip, and observed using standard dry objectives. This however does not allow slide 20 to be used at the highest possible magnifications, where it is contemplated that it will excel for its calibration functions and insights into the microscope system's image formation.

In order to use slide 20 with higher magnification microscopic systems, it is important to immersion couple the objective to slide 20. As is known, this immersion is generally accomplished using water, glycerin or another UV capable coupling fluid or a microscope immersion oil. In order for the immersion system to work properly there can be no air in the system. In these types of slides 20 however, it is important not to introduce any contaminants into slide 20 because of the tiny image features that are involved and yet a suitable homogeneous immersion system must be provided.

In order to minimize the possibility of damage to slide 20, pattern 100 is located on the inner surface of cover slip 28 and cover slip 28 is coated with a drop of the desired immersion fluid either oil or glycerin or water and then contacted to the surface of slide base 24. The resulting sandwich is then sealed around the outside with either an appropriate adhesive or epoxy, for example by adhesive ring 40. Immersion fluid which flows out from the imaging area 32 of slide 20 as cover slip 28 is affixed is received in fluid moat 36 and this prevents adhesive ring 40, or other sealing area, from being contaminated with immersion fluid.

Another means of mounting the slide 20 is to create pattern 100 on cover slip 28 and then, in a vacuum system, place cover slip 28 in the desired position on slide base 24, with pattern 100 facing slide base 24 wherein all the air within the space between cover slip 28 and slide base 24 is removed. A suitable immersion fluid can then be introduced into this space before the vacuum is removed. Alternately, cover slip 28 can be optically contacted to slide base 24 using standard methods for optical contacting so that only the high points of pattern 100 are optically contacted to slide base 24 and therefore only these points will transmit the rays of light uninterrupted. The intervening spaces will contain air, vacuum or any other gas or fluid that may be desired to enhance the contrast and assist in forming the bond between the cover slip and the base slide. This method of mounting may be used to enhance contrast of pattern 100 due to differential refraction of the optically contacted and non-contacted regions of pattern 100.

If it is desired to omit cover slip 28 from the completed slide 20, then a protective layer of suitable material can be provided over central locating and test pattern 100 on slide 20. Specifically, it is contemplated that a layer of a epoxy or cyanoacrylate can be applied by known suitable techniques such as spinning, or a layer of a glass can be applied by chemical vapor deposition, or a layer of silicon dioxide can be applied by known semiconductor fabrication techniques. As an example of such a slide 20 without a cover slip 28, pattern 100 can have a thickness (in the z-axis direction) of about two hundred nanometers and the protective layer can have a thickness of about one hundred nanometers or more, as desired.

With slide 20, it is important to carefully plan the patterns used in pattern 100 as the patterns are at least as important as the methods of production. The inclusion of regularly spaced alternating patterns of opaque and transparent bars or ruled lines in the form of grating-type structures are desirable as these types of structure have formed the basis of intercomparison in the prior art and therefore are useful to maintain a link with comparisons made in the past historical literature.

A series of circular objects or holes of descending sizes are desirable to allow the study of "airy disc" formation in the microscope optics. Other patterns including black dots in white fields, stars, irregular shapes and spaces, can also be included in order to test various aspects of image forming optical and electronic systems.

While the prior art has provided some examples of test patterns, these patterns suffer from the disadvantage that the microscopist often can not determine what he is observing without moving the field of view from the pattern being observed to indicia located outside the field of view. The necessity of moving the field of view to locate and read such indicia is inconvenient, at best, and can result in the microscopist "getting lost" on the test slide. For example, a known prior art pattern is the Siemens star yet, when used with a high power objective, such as a ×100, the star will extend outside the limits of the field of view and thus the microscopist does not necessarily have any way to determine how far within the limits of the star pattern his field of view is.

Figure 7:
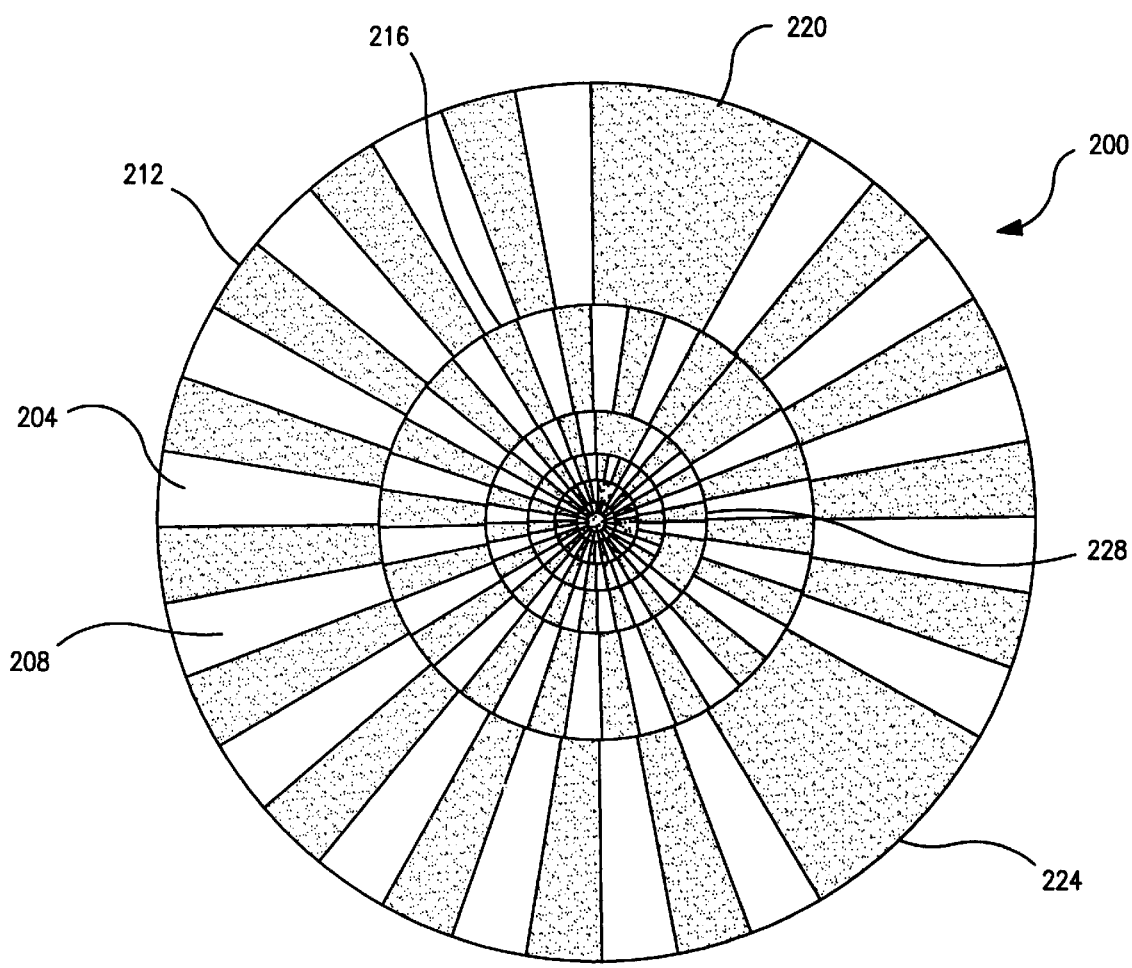
FIG. 7 shows an example of a self-identifying pattern used in an embodiment of the present invention.

To avoid or mitigate the need to move the field of view, an embodiment of the present invention employs what the present inventor refers to as "self-identifying" patterns. FIG. 7 shows a self-identifying pattern in the form of an alternating pie star 200 which has rings formed of light 204 and dark 208 pie sections. As shown, outer ring 212 has a larger diameter than the next adjacent inner ring 216 and the diameters of each succeeding inner ring continue to decrease, at a preselected rate. Identifying indicia are provided within star 200 by the alternations of the light and dark pie sections in the rings. Specifically, starting at outermost ring 212 and continuing in alternating inner rings a reference pair of triplets of dark pie sections are formed. Ring 212 includes reference triplet 220 and reference triplet 224 and, by counting the number of light pie sections 204 between reference triplets 220 and 224 (in this case five) the actual ring being observed can be determined. As shown, ring 216 does not include reference triplets but the next innermost ring 228 does and only four light pie sections are located between them. A code, supplied with the slide, will relate the number of light pie sections between reference triplets to a given set of feature sizes, including the ring diameter and the pie section sizes. In this particular example, one reference triplet is fixed at the same angular position (shown by triplet 220) while the other reference triplet is located one pair of pie sections closer to the reference triplet on each successive inner ring.

In this embodiment, the sizes of the rings are selected such that at least two rings will always be observable within the field of view of a microscope for which the pattern is intended to be used. As such, a microscopist can easily determine where he is within the pattern once he has located a pair of reference triplets in any ring.

Figure 8:
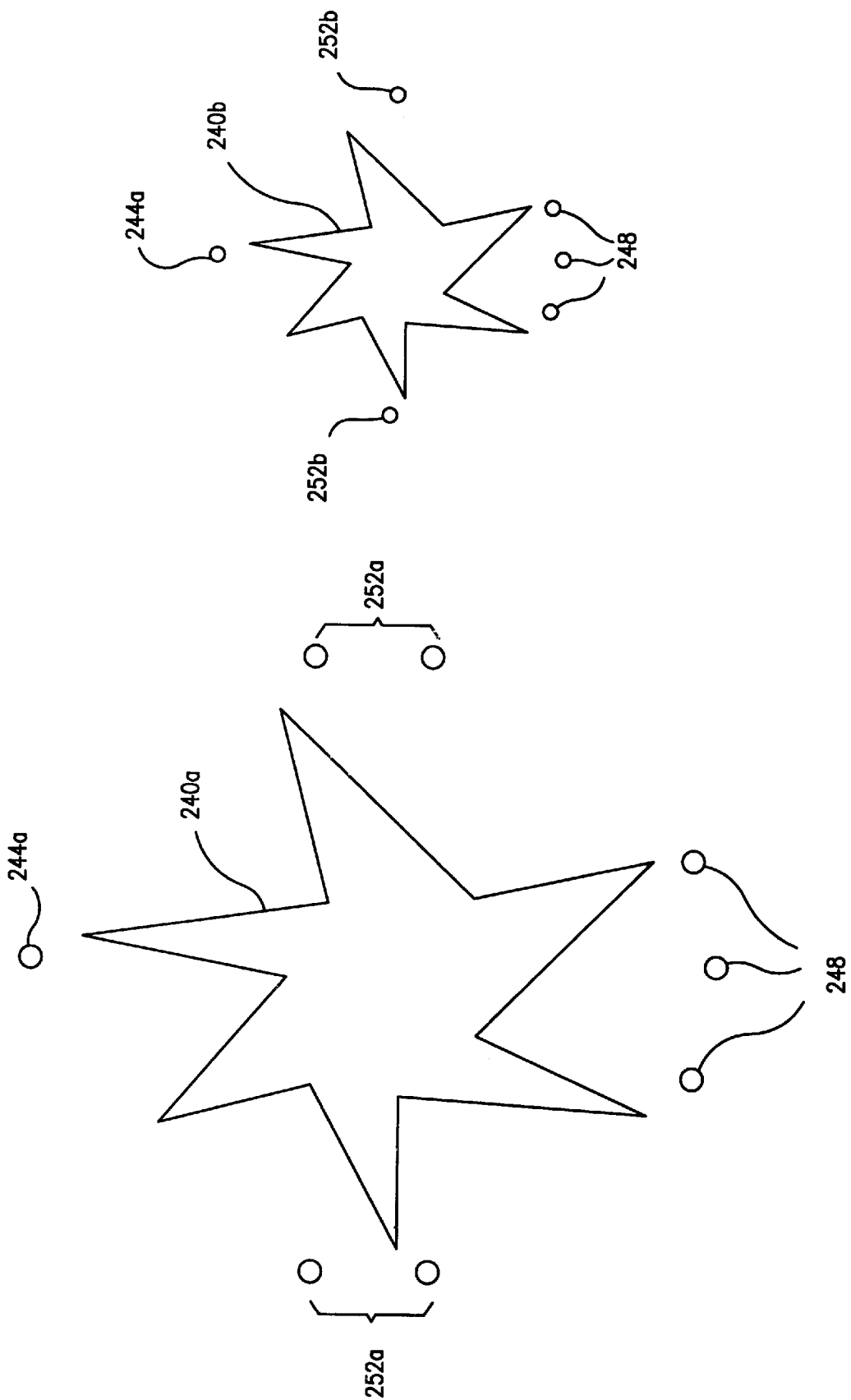
FIG. 8 shows a representation of another example of a self-identifying pattern used in an embodiment of the present invention.

FIG. 8 shows another example of a self-identifying pattern 240 for use with the present invention. In the Figure, pattern 240 is a sharp-edged geometric pattern and is shown at two different sizes 240*a* and 240*b*. While patterns 240*a* and 240*b* are identical in shape, each has associated with it a set of markers 244, 248, 252 which are positioned and sized such that, when pattern 240 occupies up to seventy five percent of the field of view of the microscope, the set of markers 244, 248 and 252 will be visible to the microscopist. To determine the size of pattern 240 under observation, the microscopist needs to locate the reference markers 244 and 248 which establish the orientation of pattern 240 (in this example marker 244 is a single dot and marker 248 is a set of three adjacent dots). Next marker 252 is examined to determine the specific pattern being observed. In FIG. 8, marker 252*a* comprises a pair of dots and marker 252*b* comprises a single square. As shown, marker 252 is repeated on each side of pattern 244. Once the microscopist identifies markers 244, 248 and 252 for a pattern 240, the size and other characteristics of the pattern 240 being observed can be determined according to a defined coding of marker 252.

As will be apparent to those of skill in the art, the self-identifying patterns shown in FIGS. 7 and 8 are but two examples and other self-identifying patterns as will occur to those of skill in the art can also be employed.

Registration numbers and authenticity markings can be employed to ensure traceability and quality assurance for each slide 20. The concept of including text labels or reference markings adjacent to image details or actually located in the image itself which provide details on the scale of the features of the image being viewed are usefull for reference and record keeping. When such reference marking are actually part of test pattern 100, the resulting record provides a relatively definitive proof of the performance of a system. When, as described below, test slide 20 includes a library of patterns such as a compendium of images of microsopcial images of bacteria or histo-pathology reference images, then slide 20 can be marked with external and/or large scale (suitable for reading with the naked eye) markings to direct the microscopist to the area containing the image information of interest.

The inclusion of reference scales is desirable to calibrate the magnification systems, but it is also possible to use reference photomicrographs of video images of the test slide as the scale reference for a series of later images of subjects all imaged under the same conditions. Slide 20 can include patterns of offset stars and checkerboards for testing flatness of field and pin cushion aberrations.

As one of the functions of slide 20 is meteorological applications in providing measurement standards and another application is providing microscope calibration tests and resolution tests, some means of calibrating and certifying slide 20 must be provided for such uses. The present inventor has considered three approaches for this particular slide 20 and the method of producing the calibrations is described as follows. This first method is in a system where a linear drive is used to produce the features in pattern 100. In other words, the linear drive is used to either scan a focused energy beam or laser, etc. or move the substrate during production. It is possible to step the structure out through a larger than normal distance, for example a distance of one centimeter, across the slide and then produce two relatively large structures at both of the two endpoints of this centimeter-long travel. These endpoints can then be used for measurement using standard comparator techniques against a known measurement standard.

The second approach is to use an area of the slide as an optical grating and to have the process technique produce a grating in the surface of the material and in doing so, the spacing of that grating area can be calibrated using light and measuring the spectral characteristics of the grating using optical methods.

The third approach is to use a calibrated scanning or transmission electron microscope where it is used to actually image the pattern on the cover slip or slide base itself or a replica of the pattern, prior to being mounted. The image from the scanning or transmission electron microscope then provides the certification of pattern 100.

The present invention is not limited to any of these three certification approaches and any other suitable approach, as can occur to those of skill in the art can be employed.

Slide 20 is designed to be used in many different types of microscopic applications. For example, slide 20 can be used in bright field microscopic work where it is used with either conventional light or UV light. In reflected light microscopy, slide 20 can be used with only the etch resist layer since the microscope will be primarily supplying information on surface features. Slides 20 for reflected light work, can employ opaque substrates such as metal plates of controlled thickness since there is no advantage to having light pass through the substrate and, in fact, light entering the substrate can result in erroneous images due to reflections from the back surface of the substrate.

In a conventional system, standard immersion oil can be used both as the coupling fluid from the objective to slide 20 and as the internal mounting fluid for cover slip 28 to slide base 24 itself. In UV work, it becomes important to use UV-coupling fluids and here distilled water can be used or glycerin or one of the other commercial UV-coupling preparations such as those expressly made for UV, such as Cargill Liquid Number 50350, sold by R. P. Cargill Laboratories Inc., 55 Commerce Road, Cedar Grove, N.J., USA. This fluid is specifically formulated for use in an all fused silica system for visible and UV illumination.

It is also contemplated that slide 20 can be used with dark field illumination techniques. In dark field illumination, it may often be sufficient just to have slide 20 prepared with the etch resist as the etch resist provides enough surface contour to provide good sharp dark field images without having to etch or metallize slide 20. For use with a scanning electron microscope use or an environmental scanning electron microscope, it may be desirable to prepare pattern 100 on the surface of the slide base 24 and not employ a cover slip 28 at all.

While in the above-mentioned embodiments of the present invention, pattern 100 is centered in image area 32, in a further embodiment of the present invention pattern 100 is formed adjacent the portion of image area 32 wherein it is desired to place a microscope specimen. Specifically, in the event that pattern 100 is formed on a coverslip 28, cover slip 28 will include an area intended to contact the specimen and pattern 100 will be located adjacent this area. It is contemplated that the central area of clover slip 28 will be intended to contact cover slip 28 and pattern 100 will be located radially outwardly from this specimen contact area. Similarly, if pattern 100 is formed on slide base 24, a portion of slide base 24 will be intended to receive the microscope specimen and pattern 100 will be formed adjacent this area. In either case, an appropriate locating pattern 108 will also be provided to assist the microscopist in shifting between pattern 100 and the microscope specimen. For large specimen areas, it is contemplated that pattern 100 can be located in the specimen area to superimpose pattern 100 onto the specimen itself. It is also contemplated that, in some circumstances, slide 20 can include two or more calibration and text patterns 100.

It is also contemplated that test slide 20 can be produced using those techniques presently used in the manufacture of compact discs ("CD's") or the like. Presently, CD's are commonly injection molded in a known injection molding configuration wherein the information to be carried by the CD is represented by a plurality of recesses located on an information carrier, commonly referred to as a "stamper", removably located in the mold. When a mold cycle is started, the mold is closed with the stamper inside the mold and liquefied plastic is injected into the mold where it contacts the stamper. The mold is then rapidly cooled, opened and the CD is ejected with a plurality of upraised "pits" in one of its surfaces, the pits corresponding to the recesses on the stamper. These pits can have sizes smaller than a micron.

As this molding technology can produce a pattern in a plastic substrate with submicron sizes, it lends itself well to the production of test pattern 100 and test slides 20 at a reasonable cost and with a high degree of reproducibility.

Conventionally, the patterns of a CD are arranged radially about the CD's surface, in a single spiral track which is read by the laser or other reading device when the CD is used. Thus, the stamper is created with the recesses in the desired spiral pattern. In contrast, in the present invention, the stamper which is employed is arranged in a different manner. Specifically, a blank stamper of the type conventionally employed in the manufacture of CD's has a desired test pattern 100 formed therein. This test pattern can be formed in a suitable manner, including ion beam machining and/or photolithographic techniques, depending upon the desired minimum size of the features of the pattern. It is also contemplated that features of different depths can be formed in the stamper, if desired, and that metallization or other suitable techniques can be employed to create upraised patterns on the stamper, instead of or in addition to the recesses described above. It is contemplated that the stamper can include a single test pattern, a repeated set of a test pattern, or a variety of test patterns, as desired.

In addition to the conventional injection molding techniques used to form CD's, it is contemplated that similar, but non-injection based, techniques can be employed. For example, it is contemplated that suitable liquid materials, such as polymers or supersaturated liquids, can be poured into a mold including a stamper or the like and allowed to cure or set. The resulting carrier is then removed from the mold. Also, it is contemplated that one or more layers of a suitable metal, silica or other material can be chemical vapour deposited onto a stamper to build the carrier, the various layers being annealed, if required. The result of this process can then be reinforced with material, such as sprayed-on or conventional metal tooling or other substances sprayed onto the carrier. When complete, the carrier and reinforcing material is removed, as a whole, from the mold. It is further contemplated that molten fused silica or other UV transmitting materials can be poured or pressed with the stamper to form a test pattern therein. This latter embodiment is particularly attractive for the manufacture of slides 20 for use with UV.

Once a suitable stamper has been created, the stamper is placed in a conventional CD manufacturing system and the conventional molding operation commenced. The resulting CD's, which now contain the test pattern, are ready for further production process steps. By combining both upraised portions and recesses on the stamper employed to make the patterns, three-dimensional features can be provided in the patterns.

Figure 10:
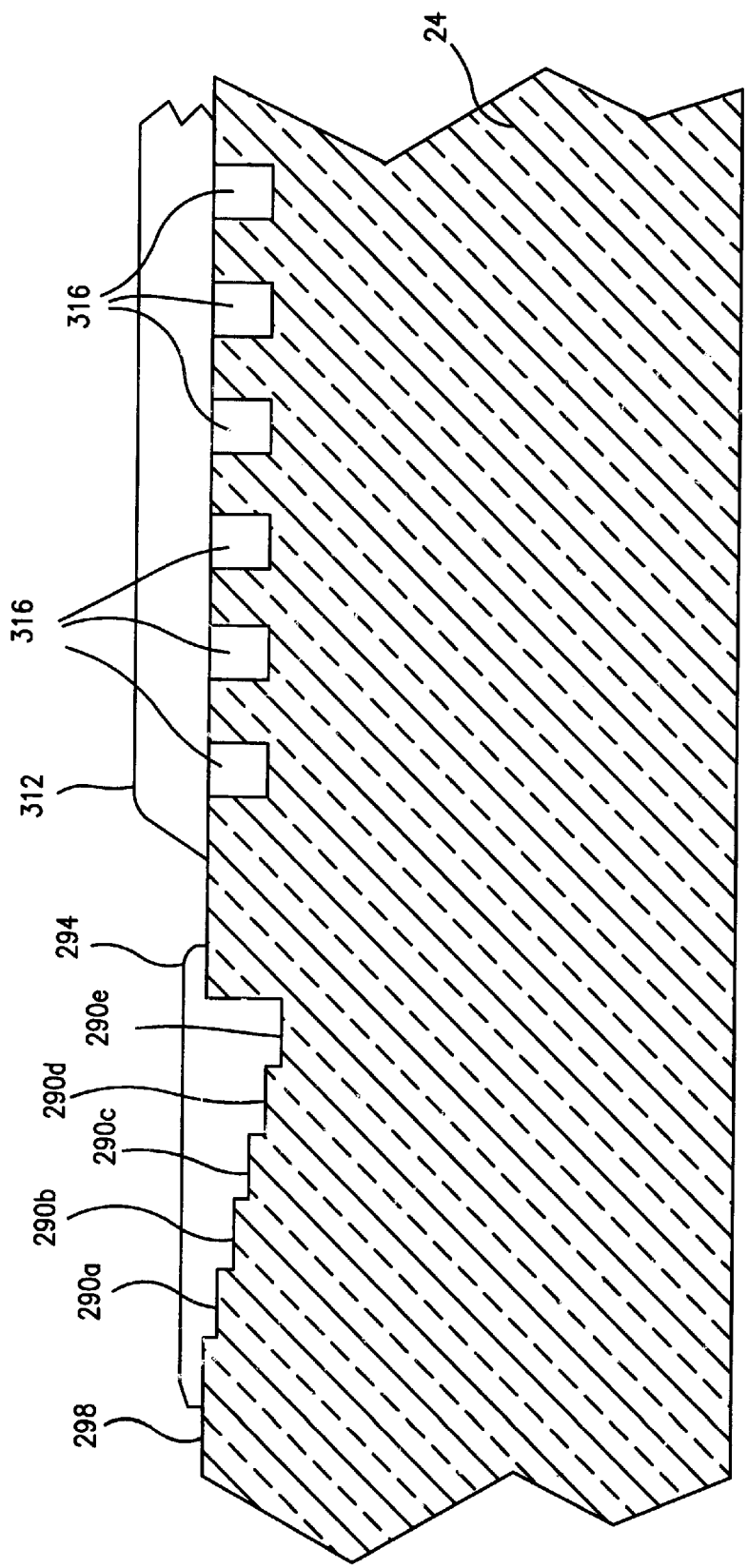
FIG. 10 shows a cross section through a test slide with three dimensional features which has been fabricated from injection molding techniques.

It is also contemplated that known diffraction and/or interference principles can be employed to create regions of controlled reference colors or image color in the resulting test pattern. A method of creating reference colors is shown in FIG. 10 wherein slide base 24 includes a terraced structure comprising five adjacent wells 29a, 290b, 290c, 290d and 290e which have been filled with a thin film coating 294 deposited on surface 298 of slide base 24 and in wells 290. As will be apparent, the different depths of wells 290 result in different thicknesses of thin film coating 294 and this results in a user perceiving different colors when viewing coating 294. As will be apparent to those of skill in the art, thin film coating can be applied as a planar coating, i.e.— with a planar upper surface, in any suitable manner as will occur to those of skill in the art to achieve the desired color or colors. In the alternative, thin film coating 294 can be applied as a non-planar coating which conforms, to at least some extent, to the surface resulting in colors characteristic to the overall thickness. FIG. 10 also shows the above-mentioned planar film coating 312 which can be employed to protect surface features 316 when a cover slip is not employed with slide base 24.

If the test slide 20 is to be used with transmitted light applications, the test pattern can be considered as being ready for use, or can be further processed, as described below. For example, contrast enhancement processes can be performed on the test pattern such as by performing conventional CD-type metalization of the surface of the CD. In this case, unlike with conventional CD's, the surface would be polished to remove the metal on the uniform reference surface of the CD (if the master pattern was formed as an upraised pattern on the stamper and is thus formed as a recess in the CD) or to remove the metal from the pattern (if the master pattern was formed as a recessed image on the stamper). In either case, a contrast enhanced pattern is obtained. A dye or ink can also be applied to the surface and wiped from the surfaces resulting in a contrast enhanced pattern. Any other contrast enhancing technique, suitable for visible light or other light wavelengths, as will occur to those of skill in the art can also be employed. If the test slide is to be used for reflected light applications, the CD surface will be coated with an appropriate layer of metal or other material using known techniques. Further, the reflectivity of the CD surface, in terms of color, absorption, and specular versus diffuse characteristics can be selected to enhance the visibility and/or appearance of the test pattern.

Whether or not a contrast enhancement step is performed, the resulting test pattern can be used as is or can have a protective overcoating applied to it. If a coating is to be applied, it will typically have a thickness on the order of several tens of microns and can be created by using chemical vapor deposition techniques to grow layers of silicon dioxide or the like, or it can be a lacquer or other known coating material. Further, the protective coating can include a dye to enhance the contrast of the test pattern. For example, a blue dye can be applied to the surface such that the pattern features are either significantly more blue (due to the increased thickness of the blue dye when the pattern features are recessed in the CD surface) or significantly less blue (due to the decreased thickness of the blue dye when the pattern features are upraised on the CD surface).

Once the processing of the CD is complete, standard printing techniques such as silk screening and the like can be employed to provide information and/or reference markings on the CD which can define the slide type, test pattern, method of application and a serial number.

Figure 9:
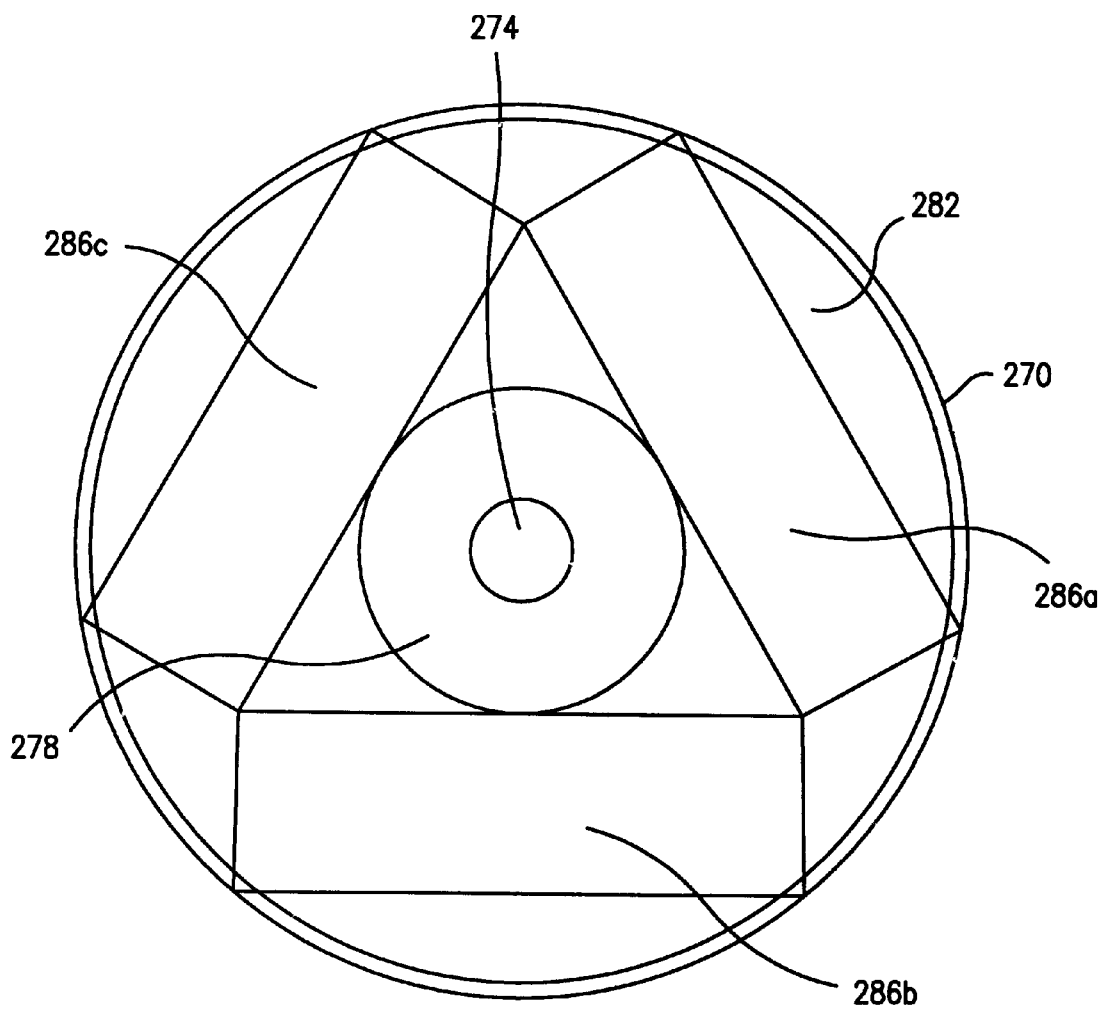
FIG. 9 shows an elevational view of a CD including test patterns in accordance with the present invention.

The resulting CD can be employed intact, and placed on the microscope stage in this form, or can be cut for use with test slides of more common size and shape. In this later case, the CD can be cut to form complete slides as shown in FIG. 9 or pattern areas can be cut from the CD and mounted to conventional slide bases. In this latter case, it is contemplated that ten or more patterns can be cut from a single CD. In FIG. 7, a CD 270 manufactured in accordance with the present invention is shown. In conventional CD manufacturing techniques, information is not formed at the center 274 of the CD or the annular region 278 adjacent it as this is where the liquefied plastic enters the mold. As shown, the remaining information/image surface 282 can be cut into three test slides 286a, 286b, and 286c. It is contemplated that, if desired, standard CD molding processes can be modified to increase the yield of test slides from the CD. For example, it is contemplated that CD's with a square or rectangular geometry can be produced, if desired.

In addition to the contemplated advantages of cost efficiencies and pattern reproducibility, it is contemplated that this embodiment of the present invention provides additional advantages in that, while test patterns as described above can be employed with these test slides, other test patterns such as reference images can also be provided for informational, educational and/or training purposes. Such reference images can include a "standard" diatom or butterfly which is life sized and includes features down to the sub-micron level. In such a case, one could look at the surface of the CD with the naked eye and perceive a butterfly, examine the CD under a low power microscope and see anatomical details of the butterfly and examine the CD under a high power microscope to see the cellular and subcellular features of the butterfly. Such images can be used as a reference, in training in microscopical technique, and for education in the recognition of microscopical features and/or objects. Other contemplated applications include the field of scientific or natural curiosities, in which case a series of images can be provided on a CD, as a library of bacteriological images which are reproductions of actual bacteria photomicrographs, etc. It is contemplated that reference images can be actual images obtained by scanning electron microscopes, scanning transmissive electron microscopes, light microscopes, traditional or digital photography, or by any other suitable means as will occur to those of skill in the art. It is further contemplated that composite or montage images can be provided wherein actual images and/or those produced by a graphics artist are combined. For example, an image of a butterfly obtained with a light microscope can be combined, at selected locations, with SEM images of fine features such as hair, eyes, muscles, cells and sub-cellular or inter-cellular systems. It is contemplated that these combinations or montages will include various images at corresponding scales, thus the image of the butterfly will be life sized, the SEM images of the hair on its wing will be life sized, the light microscope images of its cells will e life sized, etc., allowing the microscopist to "move in" or out of the image as desired.

Figure 11:
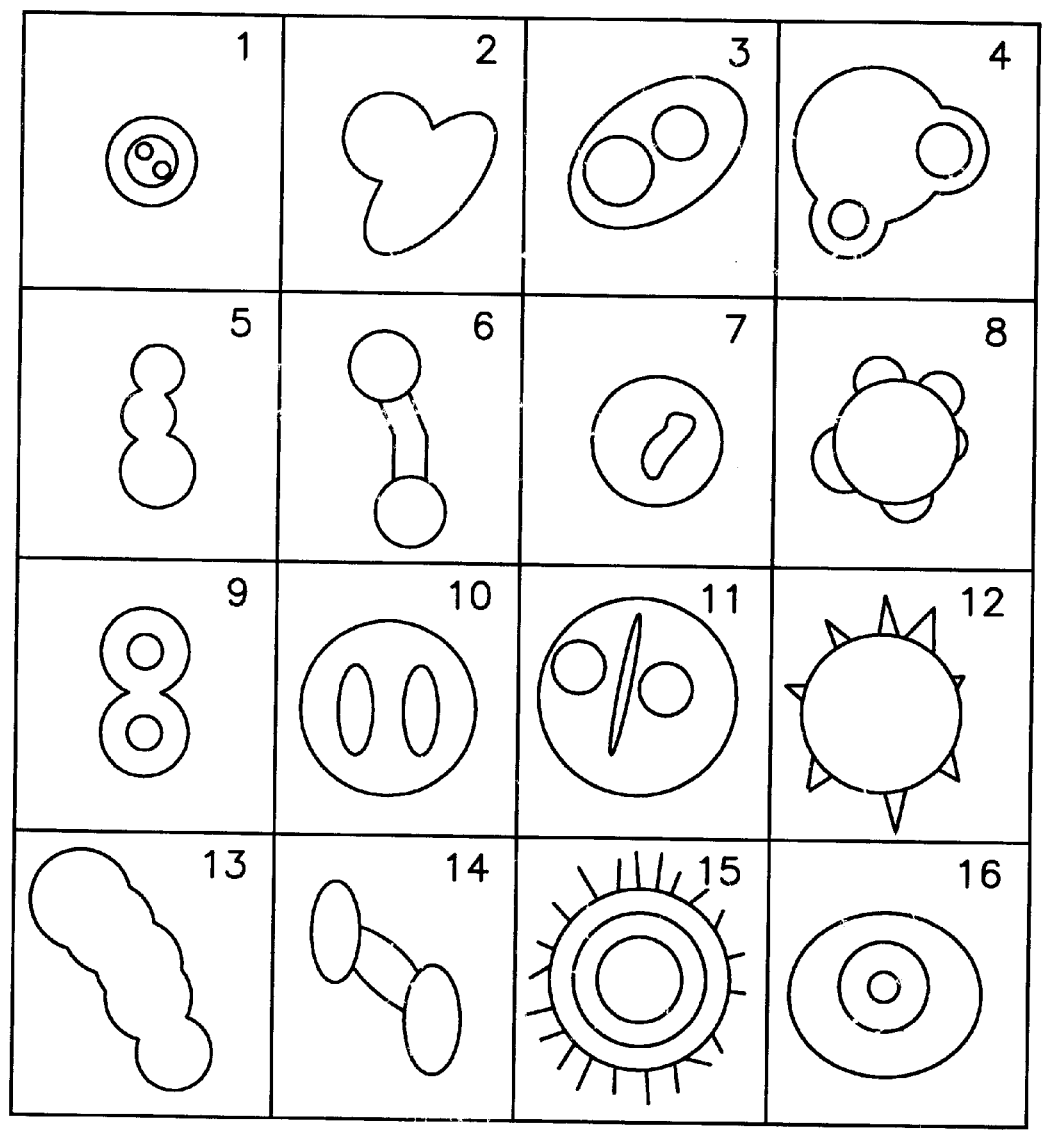
FIG. 11 shows an example of a collection of reference images for use in an embodiment of the present invention.

Another example of test patterns comprising reference patterns is the provision of libraries of reference patterns, such as a histo-pathological images for diagnostic use or a field identification manual for plants, insects or animals both of which are based upon images of actual subjects. Depending upon the subject of interest, the images can be actual size, or enlarged or reduced by a suitable scale factor. If the actual image sizes are small, i.e.—on the order of ten microns square, as will be acceptable for a typical bacteria, etc., and as the actual information surface of a conventional CD is about ten thousand, two hundred millimeters, as many as approximately one hundred and two million images of bacteria can be provided on a single CD. This example illustrates the enormous potential of the present invention to convey test patterns comprising reference images in a compact and useful form. Updates to reference images can be provided by creating a new stamper to produce new disks. Such disks can have both suitable radial indicia which are visible to the naked eye to identify regions of interest on the CD surface and indicia which can be viewed via microscope to identify specific images. Appropriate textual information can also be provided on the disk, adjacent the images, if desired. FIG. 11 shows a schematic example of a collection of sixteen images of bacteria which can be provided with the present invention. As shown, each image is surrounded by a grid to assist in locating an image and includes a reference numeral to identify each image. The reference numeral can be associated with relevant textual information which is also located on the CD to render it readily accessible to the microscopist. As will be apparent to those of skill in the art, using the 3D techniques mentioned above, the images in such collections need not be limited to two dimensional representations but can instead be three dimensional to further augment the realism of the images.

Some of the contemplated uses of providing test patterns comprising reference images include medical and biological uses wherein the compact images and the generally robust nature of the CD (compared to film, etc.) are believed to provide significant advantages. Further, nothing but a microscope is required to view the images, eliminating the need for film projectors, VCRs, computers, electrical power supplies, etc., allowing use in remote or third world environments. As the references images can be actual size (i.e.—scale of 1), this allows the microscopist to view a reference image and an actual sample on the same microscope, mitigating the effects of aberrations or distortions introduced by the microscope as this will be common to both the reference image and the sample.

As will be apparent to those of skill in the art, the only limitation on the pattern produced, beyond the inherent minimum feature size, is the ability of the manufacturer to create a stamper with the desired pattern. Thus, a wide variety of test and other useful patterns can be provided, in monochrome or color, as desired.

The present invention provides a test slide from which a comprehensive series of tests can be performed to yield information on all the various image formation properties of a microscope system when operating at the edge of the resolution limits which are normally associated with optical and UV microscopy. The present invention is also useful in confocal microscopy and in scanning electron microscopy and environmental scanning microscopy.

The above-described embodiments of the invention are intended to be examples of the present invention and alterations and modifications may be effected thereto, by those of skill in the art, without departing from the scope of the invention which is defined solely by the claims appended hereto.

What is claimed is:

1. A test slide comprising:
   a substrate;
   a test pattern formed on said substrate, said pattern comprising at least a diffraction grating and a scale system; and
   a locating pattern formed on said substrate to assist an observer to locate said test pattern,
   said test pattern including first and second diffraction gratings, said first diffraction grating being oriented orthogonally to said second diffraction grating, and first and second scale systems, said first scale system having an orientation corresponding to the orientation of said first diffraction grating and said second scale system being oriented orthogonally to said first scale system.

2. A test slide according to claim 1 wherein said test pattern further comprises header means to identify said test slide.

3. A test slide according to claim 2 wherein said means to identify includes a unique identification number for said slide.

4. A test slide according to claim 2 wherein said test pattern further comprises an offset segment pie star.

5. A test slide according to claim 4 wherein said test pattern further comprises at least one series of geometric shapes, each series comprising a geometric shape repeated in said series at different sizes.

6. A test slide according to claim 4 wherein said test pattern further comprises at least one geometric shape repeated at at least two scales, each said shape including features to self-identify the scale of the shape.

7. A test slide according to claim 6 wherein said geometric shape is an alternating pie shape.

8. A test slide according to claim 5 including at least first and second series of geometric shapes, said repeated geometric shape of said first series having different geometric properties from the repeated geometric shape of said second series.

9. A test slide according to claim 1 wherein said substrate is a slide base.

10. A test slide according to claim 1 wherein said substrate is a cover slip.

11. A test slide according to claim 10 wherein said test pattern and said locating pattern are formed on a first side of said cover slip, said cover slip being mounted to a slide base via adhesive means with said first side adjacent said slide base.

12. A test slide according to claim 11 wherein a suitable immersion fluid is maintained between said first side and said slide base.

13. A test slide comprising:
- a substrate including an image area;
- a test pattern formed on said substrate in said image area, said pattern comprising a known image having at least two features selected from the group comprising grating-type structures, scale systems, image series, offset segment pie stars and indicia to uniquely identify said slide,
- a first of said at least two features having an orientation which is substantially orthogonal to a second of said at least two features.

14. A slide according to claim 13 wherein said known image comprises first and second grating-type structures and first and second scale systems, said first grating-type structure and said first scale system having a first common orientation, said first common orientation being substantially orthogonal to a second orientation which is common to said second grating-type structure and said second scale system.

15. A slide according to claim 13 further comprising a locating pattern to assist in locating said test pattern on said slide.

16. A slide according to claim 13 wherein said substrate is a slide base.

17. A slide according to claim 13 wherein said substrate is a cover slip which is attached to a slide base.

18. A slide according to claim 13 wherein said known image is located substantially at the centre of said image area.

19. A slide according to claim 13 wherein said known image is located at a periphery of said image area.

20. A slide according to claim 19 further including a locating pattern located between the centre of said image area and said known image.

21. A test slide comprising:
- a substrate;
- a test pattern formed on said substrate, said pattern having known shape and size; and
- a protective layer on said test pattern, said layer inhibiting inadvertent damage to said test pattern and being non-opaque to an preselected range of wavelengths for which said slide is intended to be used.

22. A test slide according to claim 21 wherein said test pattern includes features which are less than one micron in size.

23. A test slide according to claim 21 wherein said protective layer is formed via chemical vapour deposition techniques.

* * * * *